(12) United States Patent
Duvvuri et al.

(10) Patent No.: US 6,214,836 B1
(45) Date of Patent: *Apr. 10, 2001

(54) WATER SOLUBLE ANALOGUES OF 20(S)-CAMPTOTHECIN

(75) Inventors: Subrahmanyam Duvvuri; Venkateswarlu Akella; Sharma Manohara Vedula; Rao Venkateswara Kalla; Srinivas S.S.V. Akella, all of Andhra Pradesh (IN)

(73) Assignees: Dr. Reddy's Research Foundation, Hyderabad (IN); Reddy Cheminor, Inc., Ridgewood, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/772,071

(22) Filed: Dec. 19, 1996

Related U.S. Application Data

(63) Continuation-in-part of application No. 08/655,259, filed on Jun. 17, 1996, now Pat. No. 6,028,173, which is a continuation-in-part of application No. 08/471,640, filed on Jun. 6, 1995, now abandoned.

(51) Int. Cl.[7] ............... A61K 31/4745; C07D 491/22; A61P 35/00; A61P 35/02

(52) U.S. Cl. ............................................. 514/283; 546/48

(58) Field of Search .................. 546/48; 514/283

(56) References Cited

U.S. PATENT DOCUMENTS

| | | | |
|---|---|---|---|
| 4,399,282 | 8/1983 | Miyasaka | 546/48 |
| 4,473,692 | 9/1984 | Miyasaka | 546/48 |
| 4,513,138 | 4/1985 | Miyasaka | 546/48 |
| 4,545,880 | 10/1985 | Miyasaka | 204/158 |
| 4,604,463 | 8/1986 | Miyasaka | 546/48 |
| 4,981,968 | 1/1991 | Wall | 544/361 |
| 5,053,512 | 10/1991 | Wani | 546/48 |
| 5,122,526 | 6/1992 | Wall | 514/253 |
| 5,391,745 | 2/1995 | Danishefsky | 546/48 |
| 5,446,047 * | 8/1995 | Danishefsky et al. | 546/48 |
| 5,468,754 | 11/1995 | Hausheer | 514/283 |
| 5,525,731 | 6/1996 | Danishefsky | 546/48 |
| 5,541,327 * | 7/1996 | Danishefsky et al. | 546/48 |

FOREIGN PATENT DOCUMENTS

| | | |
|---|---|---|
| 0074256 | 3/1983 | (EP) . |
| 2056973 | 3/1981 | (GB) . |
| 58-39683 | 3/1983 | (JP) . |
| 58-39684 | 3/1983 | (JP) . |
| 58-154584 | 9/1983 | (JP) . |
| 97 46564 * | 12/1997 | (WO) . |

OTHER PUBLICATIONS

Ykult, Chem Abstr. vol. 98 Entry 34828 abstracts JP 57–116074, 1983.*

Fukada, Chem. Abstr. vol. 108 Entry 212, 1988.*

Seigo Sawada, "Synthesis and Antitumor Activity of 20(S), Camptothecin Derivatives:Carbamate–Linked, Water–Soluble, Derivatives of 7–Ethyl–10–hydroxycamptothecin", Chem. & Pharm. Bulletin, Japan, vol. 39, No. 6, pp. 1446–1454 (1991).

Lawrence Snyder, "Synthesis of 19–Noranhydrocamptothecin Analogs Which Retain Topoisomerase I Inhibitory Function" J. Org. Chem 1994, 59, 7033–7037.

Ako Ejima, "Antitumor Agents V.[1] Synthesis and Antileukemic Activity of E–Ring–Modified (RS)–Camptothecin Analogues" Chem. Pharm. Bull. 40(3), 683–688, 1992.

Takashi Yaegashi, "Chemical Modification of Antitumor Alkaloids, 20(S)–Camptothecin and 7–Ethylcamptothecin: Reaction of the E–Lactone Ring Portion with Hydrazine Hydrate", Chem. Pharm. Bull. 41(5) 971–974 (1993).

Mansukh C. Wani, "Plant Antitumor Agents. 23.[1] Synthesis and Antileukemic Activity of Camptothecin Analogues", J. Med. Chem., 1986, 29, 2358–2363.

Robert P. Hertzberg, "Modification of the Hydroxy Lactone Ring of Camptothecin: Inhibition of Mammalian Topoisomerase I and Biological Activity", J. Med. Chem. 1989, 32, 715–720.

Yaw–Huei Hsiang, "Camptothecin Induces Protien–linked DNA Breaks via Mamalian DNA Topoisomerase I", Journal of Biological Chemistry, vol. 260, No. 27,p. 14873–14888.

(List continued on next page.)

*Primary Examiner*—Bruck Kifle

(57) ABSTRACT

Novel water soluble C-ring analogues of 20(S)-camptothecin having the general formula 1.

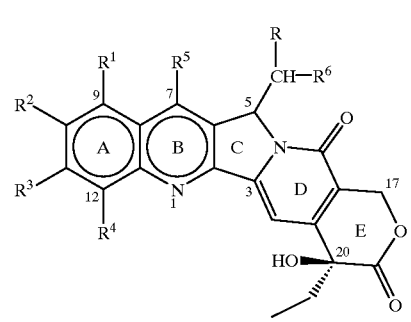

All the compounds of the formula 1 are prepared from the compounds of the general formula 2 having 20(S)-chiral carbon. The compounds of the formula 1 possess potent anti-cancer and anti-viral properties. The invention also provides an alternate process for the preparation of known C-5 substituted compounds of the formula 1.

12 Claims, No Drawings

OTHER PUBLICATIONS

Monroe E. Wall, "Pant Antitumor Agents 30[1a,b] Synthesis and Structure Activity of Novel Camptothecin Analogs" J. Med. Chem. 1993, 2689–2700.

Thomas G. Burke, "The Structural Basis of Camptothecin Interactions with Human Serum Albumin: Impact on Drug Stability" J. Med. Chem. 1994, 37, 40–46.

T. R. Govindachari, "9–Methoxycamptothecin. A New Alkaloid fromMappia foetida Miers", Indian J. Chem. vol. 10, 13–454 (1972).

Zhuo–Feng Xie, "Convergent Approach to Water Soluble Camptothecin Derivatives", Bioorganic & Medicinal Chemistry Letters, vol. 5, No. 19, pp. 2189–2194, 1995.

Biochemical Pharmacology, vol. 34, No. 8, Apr. 15, 1985, Masako Fukada et al., p. 1225–1230.

Database WPI—AN92—71412E XP002034966 JP 57116074A (Yakult Honska K.K.) Jul. 19, 1982.

Chemical Abstracts vol. 100, No. 11, Mar. 12, 1984, Abstract No. 85761a JP 58–154 583A (Yakult Co.).

Chemical Abstracts vol. 100, No. 7, Feb. 13, 1984, Abstract No. 51876f JP 58 154 584A (Yakult Co.).

English Translation JP–A–58–154584 (Yakurt Co. Ltd).

Heterocycles, vol. 38, No. 1, 1994 p. 81–94, Sugimori, et al.

Bioorganic & Medicinal Chemistry Letters. vol. 5. No. 1 pp. 77–82, 1995, Wang et al.

Chem. Pharm. Bull., vol. 39, 3183 (1991), Sawada et al.

J. Org. Chem., vol. 60, 5739–5740 (1995), Wood et al.

Chem. Pharm. Bull., 41 (2), 310–313 (1993), Yaegashi et al.

Chem. Pharm. Bull., 39, No. 10 pp. 2574–2580 (1991), S. Sawada et al.

J. Med. Chem., 34, 98–107 (1991), W.D. Kingsbury et al.

Cancer Research., 49, 5016 (1989), Covey, et al.

Cancer Research., 51, 3052 (1991), Giovanella, et al.

Biochemistry., 33, 12540 (1994), Mi et al.

* cited by examiner

WATER SOLUBLE ANALOGUES OF 20(S)-CAMPTOTHECIN

This application is a continuation-in-part of application Ser. No. 08/655,259, filed Jun. 17, 1996, now U.S. Pat. No. 6,028,173, issued Feb. 22, 2000, which is a continuation-in-part of application Ser. No. 08/471,640, filed Jun. 6, 1995, now abandoned.

The present invention relates to novel water soluble C-ring analogues of 20(S)-Camptothecin having the general formula 1.

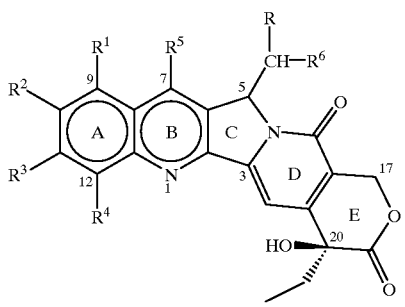

In the above formula 1, $R^1$, $R^2$, $R^3$ and $R^4$ are independently the same or different and represent hydrogen, hydroxy, lower alkoxy, aryloxy, lower alkanoyl, nitro, cyano, halo, carboxy, carbonyloxy, amino, substituted amino, lower alkyl, substituted lower alkyl or $R^2$ and $R^3$ combined together represent —O—$(CH_2)_n$—O— where n=1 or 2; $R^5$ represents hydrogen, lower alkyl, substituted lower alkyl, lower aralkyl, hydroxymethyl, carboxymethyl, aminomethyl; substituted aminomethyl where the amino group is mono or disubstituted in which both substituents are independent or combined together to form 5 or 6 membered cyclic ring system containing carbon and optionally one or two heteroatoms selected from oxygen, nitrogen and sulfur. The number of atoms in the cyclic ring system is 5 or 6.

When R represents hydrogen, $R^6$ represents lower alkoxy; carbonyloxy; cyano; nitro; thio; thioalkyl; thioaryl; amide or amino group in which the amino group can be unsubstituted, mono or disubstituted in which both substituents are independent or combined together to form a cyclic ring system of 3 to 8 atoms containing carbon and optionally one or two heteroatoms selected from oxygen, nitrogen and sulfur; phenoxy, phenyl, benzoyl or benzyl where the phenyl group can be unsubstituted or substituted with mono, di or trisubstituents which may be selected from halogen, hydroxy, alkoxy, cyano, carboxy, nitro, amido, amino or substituted amino, thioalkoxy, phenyl, benzyl, lower alkyl, or substituted lower alkyl; cycloalkyl or cycloalkyl lower alkyl where the cyclic ring may be in the range of 3 membered to 7 membered ring system containing all carbon atoms; lower alkyl groups substituted with heterocyclic rings where the heterocyclic ring system having 3 to 7 atoms contains carbons with at least one heteroatom selected from oxygen, nitrogen and sulfur, the number of atoms in the ring (s) of the heterocyclic ring system is 3 to 7; lower alkanoyl; lower alkenyl; substituted lower alkyl or substituted lower alkenyl where the substituents can be halogen, hydroxy, benzyoxy, carbonyloxy, alkoxy, aryloxy, carboxyl, cyano, thio, thioalkyl, thioaryl, aryl, heteroaryl, nitro, amido or amino in which amino group can be unsubstituted or mono, or disubstituted in which both substituents are independent or combined together to form a cyclic ring system of 3 to 8 atoms containing carbon and optionally one or two heteroatoms selected from oxygen, nitrogen and sulfur; or $R^6$ represents COOR' where R' represents hydrogen, lower allyl, substituted lower alkyl, or lower aralkyl; or when R represents lower alkyl; lower alkenyl; lower alkanoyl; substituted lower allyl; substituted lower alkanoyl; phenyl, benzyl or benzoyl in which the phenyl group may be unsubstituted or substituted; or lower alkoxycarbonyl; $R^6$ represents phenyl; benzoyl; cyano; nitro; lower alkanoyl; or COOR' group in which R' represents hydrogen, lower alkyl, lower aralkyl or substituted lower alkyl.

All the novel compounds of the formula 1 are 20(S)-isomers, substantially free from the corresponding 20(R)-isomer.

All these compounds of the formula 1 are prepared from the compounds of the general formula 12 having 20(S)-chiral carbon,

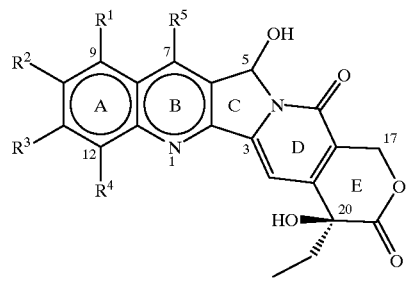

where $R^1$ to $R^5$ have the meaning described above.

20(S)-Camptothecin having the formula 2 is an alkaloid possessing strong antitumor activity,

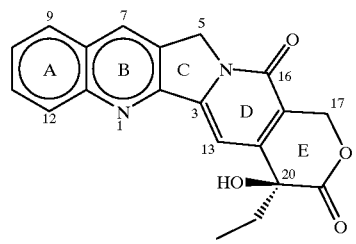

It was first isolated from the plant *Camptotheca acuminata* by Wall and co-workers in 1966. However, its development as a potential drug for cancer treatment had been abandoned due to unacceptable side effects on humans and due to its low water solubility as well as high toxicity problems. Since the discovery of its mechanism of action as an inhibitor of topoisomerise I by Liu and co-workers in 1985 [L. F. Liu, et al., *J.Biol.Chem.*, 260 14873 (1985)], the research interest on camptothecin has once again taken momentum.

To overcome this problem of low water solubility and high toxicity of camptothecin, over the last 30 years, several research groups all over the world have prepared and investigated a number of camptothecin analogues involving the modification of rings A-E or the introduction of a variety of substituents on all the five rings of camptothecin of the formula 2[M. E. Wall et al., *J.Med.Chem.*, 36, 2689 (1993); R. P. Hertzberg et al., *J. Med.Chem.*, 715 (1989); S. W. Sawada et al., *Chem.Pharm.Bull*, 41(2), 310 (1993)]. Among the various camptothecin analogues prepared to date, only two of them namely, CPT-11 having the formula 3 [*Chem.Pharm.Bull.*, 39, 1446 (1991)],

3

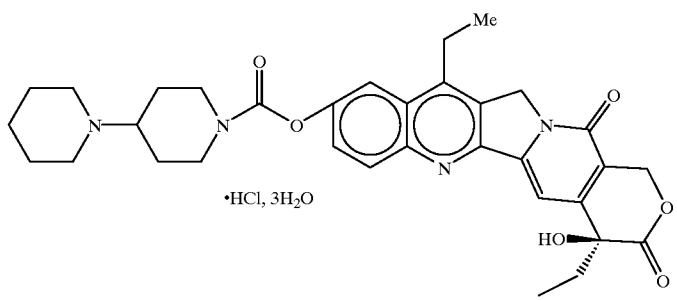

•HCl, 3H₂O

15 topotecan of the formula 4 [*J.Med.Chem.*, 34, 98(1991)]

4

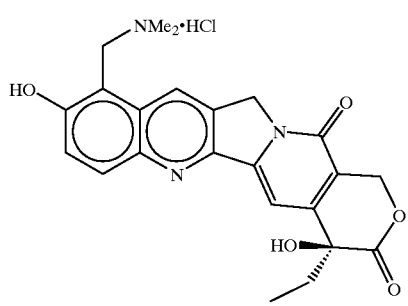

were introduced as anti-cancer drugs in the market recently. Another compound namely, 9-aminocamptothecin of the formula 5 [*J.Med.Chem.*, 29, 2358 (1986)],

5

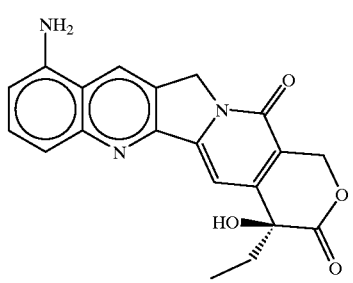

is currently undergoing phase III clinical trials. The extensively studied Structure-Activity Relationship(SAR) on camptothecin of the formula 2 [M. E. Wall et al., *J.Med.Chem.*, 36, 2689 (1993)] has revealed that 20(S)-α-hydroxy-δ-lactone (E-ring) moiety in camptothecin is essential for its activity. However, according to recent reports by Ejima et.al., replacement of hydroxyl group with an amino group at C-20 position leading to a compound such as 7-ethyl-10-methoxycamptothecin derivative of the formula 6[A. Ejima et al., *Chem. Pharm.Bull.*, 40(3), 683 (1992)],

6

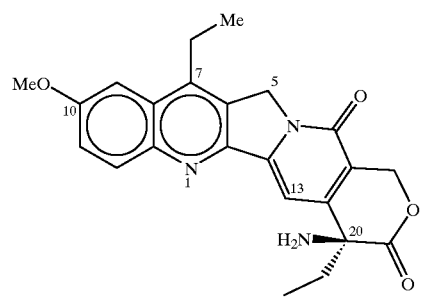

exhibited an increased in vivo antitumor activity than 20(RS)-camptothecin of the formula 7. Also in another report ( Lawrence Snyder et.al., *J. Org. Chem.*, 59, 7033 (1994)], the 18-noranhydrocamptothecin analogue of the formula 8,

7

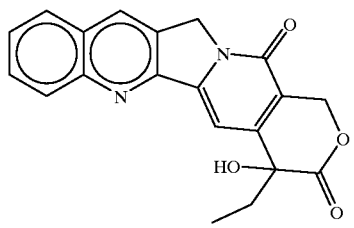

8

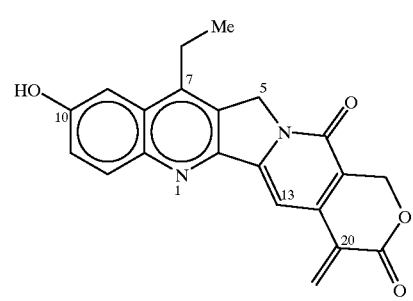

exhibited potent camptothecin like inhibition of topoisomerase I activity. Both these reports are contrary to the assumption that 20(S)-α-hydroxy functionality in camptothecin is an essential feature for its biological activity.

Based on the structure-activity results obtained for the camptothecin analogues so far prepared in the literature, it was established that the modification of substituents at C-9 and C-7 position of camptothecin of the formula 2 plays an important role in the enhancement of anticancer activity by imparting stability to the E-ring lactone [T. G. Burke et al., *J.Med.Chem* 37, 40(1994)]. It has also been recognized that the open form of the lactone moiety, namely, 'the Carboxylate form' is less effective therapeutically than the closed 'Lactone form' [Hertzberg et al., *J.Med. Chem.*, 32, 715 (1989); J. M. Covey, C. Jaxel et al., *Cancer Research.*, 49, 5016 (1989); Giovanella et al., *Cancer Research.*, 51, 3052 (1991)]. The recent studies by T. G. Burke et al., on the stability of 'closed lactone form' of various camptothecin analogues in the presence of protein called 'Human Serum Albumin'(HSA) indicated that the compounds such as CPT-11 of the formula 3 and 7-ethyl-10-hydroxycamptothecin (SN-38) of the formula 9

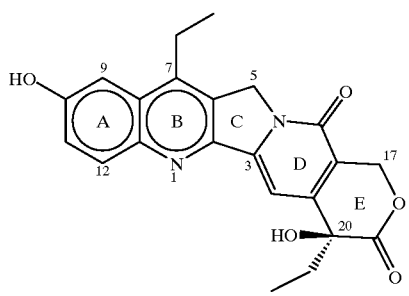

9 and Topotecan of the formula 4, in the presence of HSA at 37° C., exhibited a higher percentage (%) of lactone form at equilibrium than 20(S) camptothecin of the formula 2 and 9-aminocamptothecin of the formula 5 [T. G. Burke and Zihou Mi., *J.Med.Chem.*, 37 40 (1994); ibid., *Biochemistry.*, 33, 12540(1994)]. Based on these studies, it was recognized that the understanding of the factors influencing the lactone-carboxylate equilibrium of camptothecin analogues became an important determinant in the design of novel and therapeutically efficacious drug candidates in the camptothecin series.

Although the modification of substituents on rings A and B of camptothecin was taken up at a rapid pace to generate novel CPT analogues, ring 'C' analogues of camptothecins were limited presumably because of the research work carried out by Sawada et al., which claimed that the substituents at C-5 position of camptothecin has resulted in the reduction of anti-tumor activity of camptothecins and produced inactive analogues [Sawada S.et. al., *Chem. Pharm. Bull.*, 39(10), 2574(1991)]. The C-5 substituted camptothecins claimed by Sawada et al., (JP 58,154,584; U.S. Pat. No. 4,513,138; U.S. Pat. No. 4,473,692; U.S. Pat. No. 4,545,880; U.S. Pat. No. 4,339,282) have the structural formula 10,

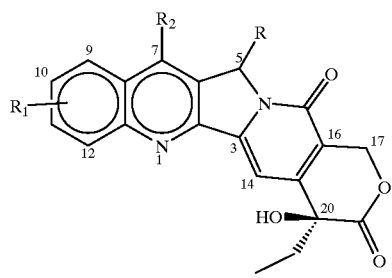

10 where R represents hydroxy, lower alkyl, lower alkoxy or acyloxy; $R^1$ represents hydrogen, methoxy at 9th position; hydrogen, hydroxy, lower alkoxy, acyloxy, SH, thioalkyl, thioacyl, nitro, amino, alkylamino, acylamino or halogen at 10th position and $R^2$ represents hydrogen, lower alkyl, lower aralkyl, $CH_2OH$, COOH, COOMe or $CH_2OR'$ where R' represents lower alkyl or acyl group.

The recent findings by K. H. Lee et al.,[*Bio.Org. MedChem.Lett.*, 5(1), 77(1995)] which includes the preparation of 5-hydroxymethyl camptothecin by the reaction of formaldehyde in N,N-dimethylformamide and 4-piperidinopiperidine on 20(S)-camptothecin, has revealed the reduced anti-tumor activity of these compounds. Also, Danishefsky et al., prepared some of the C-5 substituted 20(RS)-camptothecin derivatives by a totally synthetic approach [U.S. Pat. No. 5,391,745 and U.S. Pat. No. 5,446,047].

However, the synthetically prepared 5-substituted camptothecin derivative of the formula 11 [Terasawa et. al., *Heterocycles*, 38,81(1994)] claimed to have anti-tumor activity comparable to that of 20(S)-camptothecin.

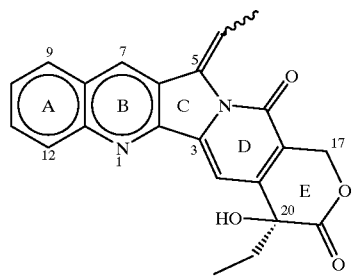

11

Keeping all these factors in mind, we focused our research studies on 20(S)-camptothecin aimed at the design of novel camptothecin analogues which can exhibit improved water solubility and improved stability of lactone form in solution. We identified an oxidative reaction in alcoholic solvents for this purpose. The resultant findings have culminated in the discovery of a novel synthetic transformation which can introduce a variety of alkoxy groups at C-5 position of 20(S)-camptothecins of the formula 14,

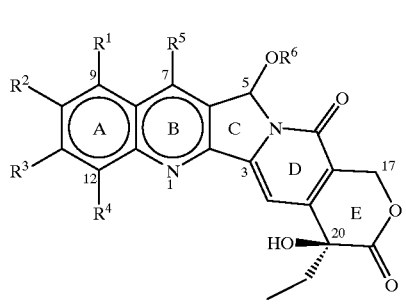

14 where $R^1$ through $R^6$ have the meaning described above, the subject matter of which was described in our co-pending application for patent bearing Ser. No. 08/771,391, There is provided a process for the preparation of the compounds of the formula 14,

14

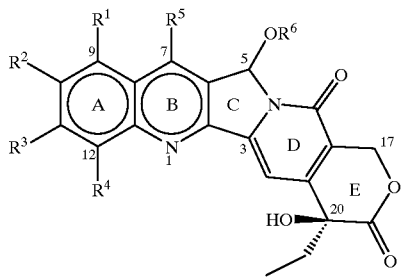

wherein $R^1$, $R^2$, $R^3$, $R^4$ are independently the same or different and represent hydrogen, hydroxy, aryloxy, lower alkoxy, lower alkanoyl, nitro, cyano, halo, carboxy, carbonyloxy amino, substituted amino, lower alkyl, substituted lower alkyl or $R^2$, $R^3$ together represent —O—$(CH_2)_n$—O— where n=1 or 2; $R^5$ represents hydrogen, lower alkyl, substituted lower alkyl, lower aralkyl, hydroxymethyl, carboxymethyl, aminomethyl, substituted aminomethyl where the amino group may be mono or disubstituted in which both substituents are independent or combined together to form a cyclic ring system of a total of 5–6 atoms containing carbon and optionally one or two heteroatoms selected from oxygen, nitrogen or sulfur; and $R^6$ represents hydrogen; phenyl or benzyl where the phenyl group may be unsubstituted or substituted with mono, di or trisubstituents which may be selected from halogen, hydroxy, lower alkoxy, cyano, carboxyl, nitro, amino or substituted amino, lower alkyl, substituted lower alkyl; cycloalkyl or cycloalkyl lower alkyl where the cyclic ring is in the range of 3 membered to 7 membered ring system containing all carbon atoms; lower alkyl groups substituted with heterocyclic rings where the heterocyclic ring system has a total of 3 to 7 atoms, the ring system contains carbon with at least one heteroatom such as oxygen, nitrogen or sulfur; lower alkanoyl; benzoyl where the phenyl group can be unsubstituted or substituted; lower alkenyl; lower alkyl; substituted lower alkyl, substituted lower alkenyl or substituted lower alkanoyl where the substituents can be halogen, hydroxy, lower alkoxy, aryloxy, thio, thioalkyl, thioaryl, aryl or hetercaryl, carboxy, cyano, nitro, amido or amino in which the amino group can be unsubstituted or mono, or disubstituted in which both substituents are independent or combined together to form 5 or 6 membered cyclic ring system containing carbon, and optionally contains one or two heteroatoms selected from oxygen, nitrogen or sulfur, the total number of atoms in the cyclic ring system being 5 or 6; with the proviso that (i) when $R^1$ is methoxy group, $R^6$ is not hydrogen or lower alkyl group; (ii) when $R^2$ is hydroxy, lower alkoxy, thioalkyl, nitro, amino, alkylamino, acylamino, and halogen, $R^6$ is not hydrogen or lower alkyl group; (iii) when $R^5$ is lower alkyl, lower aralkyl, $CH_2OH$, COOH, COOMe, or $CH_2OR''$ where R'' represents lower alkyl or acyl group, $R^6$ is not hydrogen or lower alkyl group (iv) when $R^1$ is methoxy group, $R^2$ is hydroxy, lower alkoxy, thioalkyl, nitro, amino, alkylamino, acylamino, or halogen, $R^5$ is lower alkyl, lower aralkyl, $CH_2OH$, COOH, COOMe or $CH_2OR''$ where R'' represents lower alkyl or acyl group, $R^6$ is not hydrogen or lower alkyl group; (v) when $R^1$ through $R^5$ represent hydrogen, $R^6$ is not hydrogen or lower alkyl group, which comprises, (i) reacting the compounds of the formula 16,

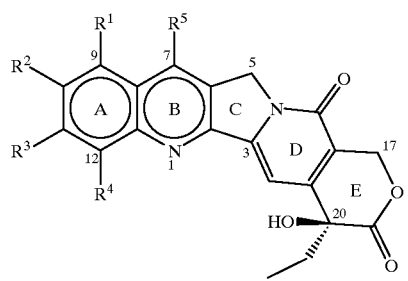

where $R^1$ to $R^5$ have the meaning described above, in the presence of an acid and an oxidizing agent which is a ferric salt, with a compound having the formula $R^6$—OH where $R^6$ represents lower alkyl, lower alkenyl, $(C_3-C_7)$cycloalkyl, haloalkyl or hydroxyalkyl, to obtain compounds of the formula 12 and compounds of the formula 17,

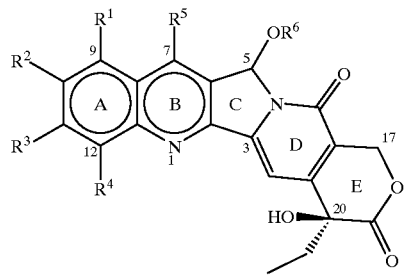

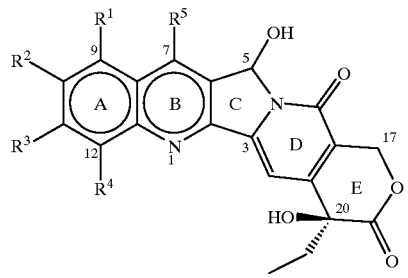

wherein $R^1$, $R^2$, $R^3$, $R^4$, $R^5$ have the meaning given above, (ii) separating the compounds of the formulae 12 and 17 prepared in the step (i), by conventional methods, (iii) hydrolyzing the compounds of the formula 17, by conventional methods, to obtain additional amounts of the compounds of the formula 12, (iv) reacting the compound of the formula 12, in the presence of an acid, with a compound having the formula $R^6$—OH to obtain compounds of the formula 14, where $R^1$, $R^2$, $R^3$, $R^4$ and $R^5$ have the meaning described above and $R^6$ is as defined above.

Functional group transformation of these 5-alkoxy camptothecins of the formula 14 produced a wide variety of novel C-5 -C-substituted 20(S)-camptothecins analogues of formula 1, which forms the subject matter of the present invention.

Hence, the discovery led to a facile and versatile semi-synthetic methodology by which virtually every camptothecin derivative known in the literature can be transformed into a variety of C-5 substituted camptothecin analogues. In another co-pending application for patent bearing application Ser. No. 08/771,390, we have described and claimed the compounds of the formula 15,

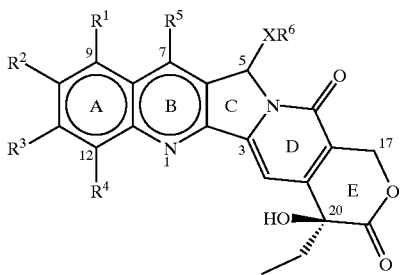

where X represents NH or NR groups.

Therefore, the present invention provides a novel process for the preparation of various C-5-C-substituted 20(S)-camptothecin derivatives of the formula 1 where $R^6$ has the meaning described above, starting from the compounds of the formula 12,

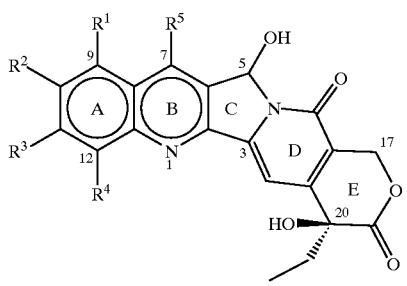

where $R^1$ through $R^5$ have the meaning described above. Furthermore, the vast variety of substituents on A, B and C rings represented by the compounds of formula 1 possess improved water solubility ranging from 1 mg to 5 mg per ml. All of the compounds prepared by the, present invention exhibited significant in vitro anti-tumor activity against a wide range of human tumor cell lines.

DETAILED DESCRIPTION OF THE INVENTION

The present invention particularly provides C-5-C-substituted water soluble analogues of 20(S)-Camptothecin having the formula 1,

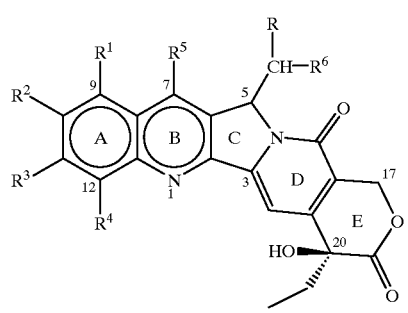

wherein the groups R, $R^1$, $R^2$, $R^3$, $R^4$, $R^5$ and $R^6$ have the meaning described above. Throughout the present invention, the terms representing R, $R^1$–$R^6$ in these compounds have the following definitions.

The term 'lower alkyl' denotes a univalent, branched or straight hydrocarbon chain containing 1 to 8 carbon atoms. Representative examples of the alkyl groups are methyl, ethyl, propyl, isopropyl, butyl, sec.butyl, tert.butyl, pentyl, isopentyl, tert. pentyl, hexyl, isohexyl and octyl.

The term 'lower alkenyl' represents a branched or straight hydrocarbon chain having sp or $sp^2$ carbon centers containing 1 to 8 carbon atoms. Representative examples of the alkenyl groups are vinyl, propenyl, butenyl, pentenyl, isopropenyl, isobutenyl, proparginyl, hexenyl and octenyl.

The term 'halogen' or 'halo' represents chlorine, bromine or fluorine. The term 'haloalkyl' denotes alkyl groups substituted with halogens, preferably fluorine, bromine or chlorine. Representative examples of the haloalkyl groups are chloroethyl, bromopropyl, fluoroethyl, trifluoroethyl, trichloroethyl and trifluorobutyl.

The term 'lower alkoxy' denotes lower alkyl groups as defined above attached via oxygen linkage to the rest of the molecule. Representative examples of those groups are methoxy, ethoxy, isopropoxy, tert.butoxy, hexoxy, heptoxy and octoxy.

The term 'lower alkanoyl' denotes lower alkyl or lower alkenyl groups as defined above attached via a carbonyl group to the rest of the molecule. Representative examples of those groups are acetyl, propionyl, propenoyl, crotanoyl, butanoyl, pentanoyl and isopentanoyl.

The term 'aminoalkyl' represents the lower alkyl groups as defined above substituted with amino groups. Representative examples of the aminoalkyl groups are 2-aminopropyl, 4-aminobutyl and 5-aminopentyl. The amino groups may also be mono or disubstituted and representative examples of these substituted amino groups are dimethylamino, diethylamino, dibenzylamino, ethylisopropylamino, pyrrolidino, piperidino, morphilino and piperizino.

The term 'heteroatom' refers to oxygen, nitrogen or sulfur. The term 'aryl' or 'heteroaryl' represents groups of aromatic nature having 5 or 6 membered rings which may be selected from phenyl, biphenyl, naphthyl, pyridyl, quinoline, isoquinoline, indole, pyroll, faran, benzofuran, thiophene, pyrimidine, thiazolidine and imidazole.

The term 'substituted phenyl' group used in the present invention refers to phenyl groups substituted with substituents which can be selected from the groups such as hydroxyl, lower alkyl, haloalkyl, phenyl, benzyl, halogen, lower alkoxy, thioalkoxy, benzyloxy, carboxyl, cyano, nitro, amido, amino, and alkylamino. Examples of such groups are 4-hydroxyphenyl, 3-methoxyphenyl, 4-fluorophenyl, 4-trifluoromethylphenyl, N,N-dimethylaminophenyl and 4-carbomethoxyphenyl.

The term 'substituted alkyl' group used in the present invention refers to alkyl groups substituted with substituents which can be selected from the groups such as hydroxyl, alkyl, haloalkyl, phenyl, benzyl, halogen, alkoxy, thioalkoxy, benzyloxy, carboxyl, carbonyloxy, cyano, nitro, amido, amino and alkylamino. Examples of such groups are fluoroethyl, chloropropyl, hydroxyethyl, methoxypropyl, N,N-diethylaminoethyl, N-benzoylaminopropyl, trifluoroethoxyethyl, phenoxyethyl, carbomethoxyethyl, (p-fluorobenzoyloxy)ethyl, aminopropyl and 2-thioethyl.

The term 'substituted amino' group used in the present invention refers amino groups substituted with substituents which can be selected from the groups such as hydroxyl, alkyl, haloalkyl, benzyl, benzoyl, alkoxy, carboxyl, amido, amino, and alkylamino. Examples of such groups are N,N- diethylamino, N-benzoylamino, N-methoxyamino, N-carboethoxyamino, and N-chloroethylamino groups. Also, both the substituents on the amino group can be combined together to form 5 or 6-membered cyclic ring system represented by pyrrolidino, piperidino, piperizino, morphilino, imidazolino, or thiazolidino.

In our copending application Ser. No. 07/771,391, Attorney Docket No. U 011024-5 we have described and claimed the compounds of the formula 12 and the process for their preparation,

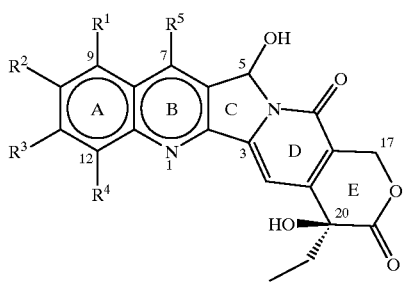

12 where $R^1$, $R^2$, $R^3$ and $R^4$ are independently the same or different and represents hydrogen, hydroxy, lower alkoxy, aryloxy, lower alkanoyl, nitro, cyano, halo, carboxy, carbonyloxy, amino, substituted amino, lower alkyl, substituted lower alkyl or $R^2$ and $R^3$ combined together represent —O—$(CH_2)_n$—O— where n=1 or 2; $R^5$ represents hydrogen, lower alkyl, substituted lower alkyl, lower aralkyl, hydroxymethyl, carboxymethyl, aminomethyl or substituted aminomethyl where the amino group is mono or disubstituted in which both substituents are independent or combined together to form 5 or 6 membered cyclic ring system containing carbon and optionally one or two heteroatoms selected from oxygen, nitrogen and sulfur. Employing the compounds of the formula 12, we have prepared the compounds of the formula 1 as described in the present invention.

Accordingly the present invention also provides a process for the preparation of the compounds of the general formula 1,

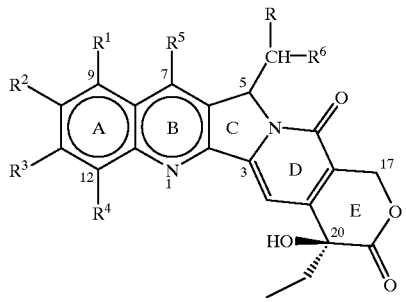

1 wherein $R^1$, $R^2$, $R^3$ and $R^4$ are independently the same or different and represent hydrogen, hydroxy, lower alkoxy, aryloxy, lower alkanoyl, nitro, cyano, halo, carboxy, carbonyloxy, amino, substituted amino, lower alkyl, substituted lower alkyl or $R^2$ and $R^3$ combined together represent —O—$(CH_2)_n$—O— where n=1 or 2; $R^5$ represents hydrogen, lower alkyl, substituted lower alkyl, lower aralkyl, hydroxymethyl, carboxymethyl, aminomethyl, substituted aminomethyl where the amino group is mono or disubstituted in which both substituents are independent or combined together to form 5 or 6 membered cyclic ring system containing carbon, and optionally contains one or two heteroatoms selected from oxygen, nitrogen and sulfur. The number of atoms in the cyclic ring system is 5 or 6.

When R represents hydrogen, $R^6$ represents lower alkoxy; carbonyloxy; cyano; nitro; thio; thioalkyl; thioaryl; amide or amino group in which the amino group can be unsubstituted or mono or disubstituted in which both substituents are independent or combined together to form a cyclic ring system of 3 to 8 atoms containing carbon and optionally one or two heteroatoms selected from oxygen, nitrogen and sulfur; phenoxy, phenyl, benzoyl or benzyl where the phenyl group can be unsubstituted or substituted with mono, di or trisubstituents which may be selected from halogen, hydroxy, alkoxy, cyano, carboxy, nitro, amido, amino or substituted amino, thioalkoxy, phenyl, benzyl, lower alkyl or substituted lower alyl; cycloalkyl or cycloalkyl lower alkyl where the cyclic ring may be in the range of 3 membered to 7 membered ring system containing all carbon atoms; lower alkyl groups substituted with heterocyclic rings where the heterocyclic ring system having 3 to 7 atoms contains carbons with at least one heteroatom selected from oxygen, nitrogen and sulfur; lower alkanoyl; lower alkenyl; substituted lower alkyl or substituted lower alkenyl where the sijbstituents can be halogen, hydroxy, benzoxy, carbonyloxy, alkoxy, aryloxy, carboxyl, cyano, thio, thioalkyl, thioaryl, aryl, heteroaryl, nitro, amido or amino in which amino group can be unsubstituted or mono, or disubstituted in which both substituents are independent or combined together to form a cyclic ring system of 3 to 8 atoms containing carbon and optionally one or two heteroatoms selected from oxygen, nitrogen and sulfur, or $R^6$ represents COOR' where R' represents hydrogen, lower alkyl, substituted lower allyl or lower aralkyl; when R represents lower alkyl; lower alkenyl; lower alkanoyl; substituted lower alkyl; substituted lower alkanoyl; phenyl, benzyl or benzoyl in which the phenyl group may be unsubstituted or substituted; or lower alkoxycarbonyl; $R^6$ represents phenyl; benzoyl; cyano; nitro; lower alkanoyl or COOR' group in which R' represents hydrogen, lower alkyl, lower aralkyl or substituted lower alkyl which comprises, i) reacting the compounds of the formula 12,

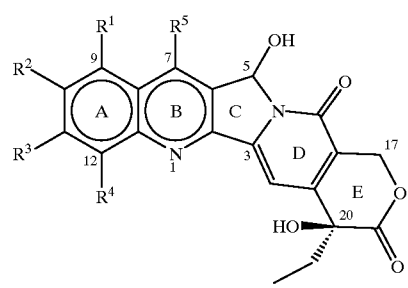

12 where $R^1$ through $R^5$ have the meaning described above 1, with a compound of the formula $R^6$—$CH_2$—J where $R^6$ represents lower alkyl, substituted lower alkyl, cycloalkyl, cycloalkyl lower alkyl, lower alkanoyl, lower alkenyl, cyano, nitro, thio, thioalkyl, thioaryl, phenoxy, phenyl, benzyl or benzoyl or COOR' group in which R' denotes lower alkyl or aralkyl group and J represents halogen, trialkylsilyl, trialkyltin, triphenylphosphonium salt or its derivative, trialkyl phosphonium salt or its derivative or J may represent MgG where G denotes halogen other than fluorine, in the presence of suitable acid or base or a metal such as lithium or zinc, as per the reaction conditions, to obtain compounds of the formula 13,

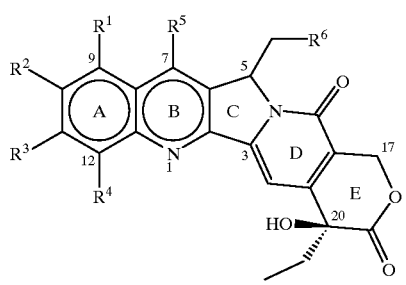

where $R^1$, $R^2$, $R^3$, $R^4$, $R^5$ and $R^6$ have the meaning given above, (ii) reacting the compounds of the formula 13 where $R^1$ through $R^5$ have the meaning described above and $R^6$ represents COOR' where R' denotes lower alkyl groups with an inorganic base followed by acidification to obtain the compounds of the formula 13,

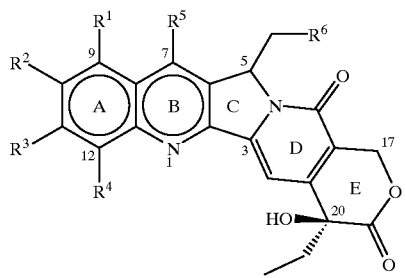

where $R^1$ through $R^5$ have the meaning described above and $R^6$ denotes COOH group;

(iii) reacting the compounds of the formula 13, where $R^1$ through $R^5$ have the meaning described above and $R^6$ denotes COOH group, with compounds of the formula R'—OH where R' represents lower alkyl, aralkyl, haloalkyl, hydroxyalkyl, alkoxyalkyl or aminoalkyl, in the presence of an acid to obtain the compounds of the formula 13,

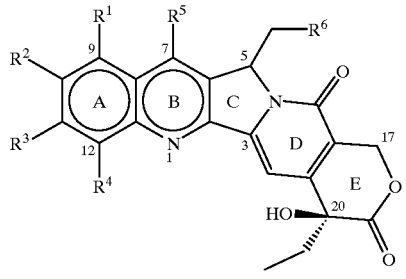

where $R^1$ through $R^5$ have the meaning described above and $R^6$ denotes COOR' group in which R' represents lower alkyl, aralkyl, haloalkyl, hydroxyalkyl, alkoxyalkyl or aminoalkyl;

(iv) reacting the compounds of the formula 13, where $R^1$ through $R^5$ have the meaning described above and $R^6$ denotes COOH group, with amines having the formula $NHR^7R^8$, where $R^7$ and $R^8$ are independently the same or different and represent hydrogen, lower alky, haloalkyl, hydroxyalkyl or aminoalkyl or $R^7$ and $R^8$ are combined together to form a 5 to 8 membered cyclic ring system containing carbon, and at least one heteroatom selected from oxygen, sulfur or nitrogen to obtain the corresponding amides of the formula 13,

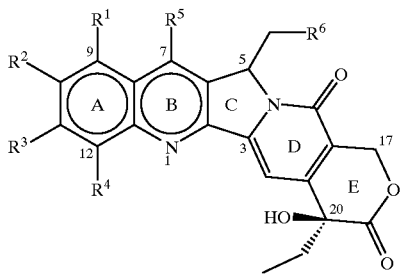

where $R^1$ through $R^5$ have the meaning described above and $R^6$ denotes $CONR^7R^8$ group where $R^7$ or $R^8$ are independently the same or different and represent hydrogen, lower alkyl, haloalkyl, hydroxyalkyl or aminoalkyl or $R^7$ and $R^8$ combined together to form a 5 to 8 membered cyclic ring system containing carbon and at least one heteroatom selected from oxygen, sulfur or nitrogen;

(v) reacting the compounds of the formula 13 where $R^6$ represents phenyl, benzoyl, cyano, nitro, lower alkanoyl or COOR' group in which R' denotes hydrogen, substituted lower alkyl, lower alkyl, or aralkyl, or a group $NR^7R^8$ where $R^7$ and $R^8$ have the meaning described in step (iv), in the presence of a base, with a reagent having the formula R—G where R is not hydrogen and G represents halogen to obtain compounds of the formula 1,

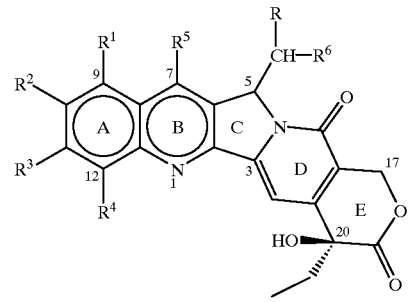

where R represents lower alkyl, substituted lower alky, lower alkenyl, lower alkanoyl, substituted lower alkanoyl, phenyl, benzyl or benzoyl in which the phenyl group may be unsubstituted or substituted and $R^1$ through $R^5$ have the meaning described above.

Accordingly, for the first time a process for the preparation of C-5 substituted camptothecin derivatives of the formula 1, starting from the compounds of formula 12 using a semi-synthetic approach has been developed. The compounds of the formula 1 prepared by the process of the present invention thus represents diastereomers containing the newly created C-5 chiral center. Indeed, the compounds of the general formula 1 are isolated as a mixture of 20(S),5(R) and 20(S),5(S) diastereomers. However, by the application of conventional analytical techniques, the two diastereomers have also been separated into their single optically pure entities.

In general, compounds of the formula 1 where R, $R^1$, $R^2$, $R^3$, $R^4$, $R^5$ and $R^6$ have the meaning described above, may be synthesized starting from the compounds of the formula 12 following the process described in the present invention and can be illustrated with the examples described in the Examples Section.

According to the process of the present invention, C-5 substituted carbon derivatives having the formula 13 can be prepared by reacting the compounds of the formula 12 where $R^1$ to $R^5$ have the meaning given above, with a compound of the formula $R^6$—$CH_2$—J where $R^6$ represents lower alkyl, substituted lower alkyl, cycloalkyl, cycloalkyl lower alkyl, lower alkanoyl, lower alkenyl, cyano, nitro, thio, thioalkyl, thioaryl, phenoxy, phenyl, benzyl, benzoyl or COOR' group in which R' represents lower alkyl or lower aralkyl groups and J represents halogen, trialkylsilyl, trialkyltin, triphenylphosphonium salt or its derivative, trialkylphosphonium salt or its derivative or J can also represent Mg—G where G denotes halogen other than fluorine, in the presence of suitable acid or base or a metal such a lithium, sodium or zinc as per the reaction conditions. The acid used in the reaction may be selected from mineral acids such as hydrochloric acid, sulfuric acid or Lewis acids such as $BF_3$-etherate, titanium tetrachloride, tin chloride, zinc chloride or stannous chloride. The base used in the reaction may be selected from sodium hydride, potassium hydride, sodium carbonate, potassium carbonate, pyridine, triethylamine, N,N-diisopropylethylamine, N-N-dimethylaminopyridine, dicyclohexyl-carbodiimide, hexamethyldisilazane, lithium bases such as n-butyl lithium, sec.butyl lithium, lithiumhexamethyldisilazide, lithium diisopropylamide or sodium methoxide, potassium tert. butoxide, or sodium tert.amyloxide. The solvent used in the reaction may be selected from hexane, benzene, toluene, ether, tetrahydrofuran, dimethoxyethane, dichloromethane and chloroform. The reaction can be performed at a temperature in the range of –100° C. to +100° C., preferably in the range of –70° C. to +80° C.

In the step(ii), the compounds of the formula 13 where $R^1$ through $R^5$ have the meaning described above and $R^6$ represents COOR' where R' denotes lower alkyl groups were reacted with an organic base followed by an acid work up to obtain the compounds of the formula 13, where $R^1$ through $R^5$ have the meaning described above and $R^6$ denotes COOH group. The inorganic base used in the reaction may be selected from sodium hydroxide, potassium hydroxide, lithium hydroxide or carbonates such as potassium carbonate, sodium carbonate, or lithium carbonate dissolved in aqueous medium. The reaction can be performed at a temperature in the range of 20° C. to 100° C.

To obtain the compounds of the formula 13, where $R^6$ represents COOR' in which R' denotes lower alkyl, arylalkyl, haloalkyl, hydroxyalkyl, alkoxyalkyl, aminoalkyl, the compounds of the formula 13 where $R^1$ through $R^5$ have the meaning described above and $R^6$ represents COOH group are reacted with compounds of the formula R'—OH where R' represents lower alkyl, arylalkyl, haloalkyl, hydroxyalkyl, alkoxyalkyl or aminoalkyl, in the presence of an acid as step (iii) of the present invention. The acid used in the reaction may be selected from mineral acids such as hydrochloric acid, sulfuric acid or Lewis acids such as $BF_3$-etherate, titanium tetrachloride, tinchloride, zinc chloride or stannous chloride. The solvent used in the reaction may be selected from benzene, toluene, tetrahydrofuran, dimethoxyethane, dioxane, dichloroethane, dichloromethane or chloroform. The reaction can be performed at a temperature in the range of 0° C. to 100° C., preferably in the range of 25° C. to 80° C.

Similarly in step (iv) of the process of the present invention, to obtain the compounds of the formula 13, where $R^6$ represents amide groups such as $CONR^7R^8$ where $R^7$ or $R^8$ are independently the same or different and represent hydrogen, lower alkyl, haloalkyl, hydroxyalkyl or aminoalkyl or $R^7$ and $R^8$ combined together form a 5 or 6 membered cyclic ring system containing carbon and at least one oxygen or nitrogen atom, the compounds of the formula 13 were reacted with primary or secondary amines. The amines used in the present invention may be selected from methylamine, ethylamine, diethylamine, dimethylamine, pyrrolidine, piperidine, morpholine, piperizine, imadazole and pyrazine. The solvent used in the reaction may be selected from benzene, toluene, tetrahydrofuran, dimethoxyethane, dioxane, dichloroethane, dichloromethane or chloroform. The temperature used in the reaction may be in the range of 20° C. to 100° C., preferably in the range of 25° C. to 80° C.

Finally, the compounds of the formula 1 can be prepared as stated in the step(v) of the process of the present invention by reacting the compounds of the formula 13 where $R^6$ represents groups such as phenyl, benzoyl, cyano, nitro, lower alkanoyl or COOR' where R' denotes hydrogen, lower alkyl, substituted lower alkyl or aralkyl, in the presence of a base, with reagents having the formula R-G where G represents halogen and R has the meaning other than hydrogen as described above. The base employed in the reaction may be organic bases such as sodium hydride, potassium hydride, lithium bases such as n-butyl lithium, sec.butyl lithium, lithiumhexamethyldisilazide, lithium diisopropylamide or alkoxides such as sodium methoxide or potassium tert.butoxide. The solvent used in the reaction can be selected from diethylether, tetrahydrofuran, dimethoxyethane, benzene, toluene, methanol, ethanol or tert.butanol. The reaction can be effected at temperatures ranging from –78° C. to +80° C.

Thus, the present invention is of particular significance in developing 5-C-substituted 20(S)-camptothecin derivatives as a new class of C-ring modified camptothecin analogues which are useful as anti-tumor and/or anti-viral agents. The present invention is also of particular significance as the process developed and described here is highly versatile and amenable for large scale preparation of these camptothecin derivatives having the general formula 1.

The methodology developed and described in the present invention will provide access to a wide variety of C-5-Carbon substituted C-ring analogues having diverse substituents on rings A and B of 20(S)-camptothecin. Some of the preferred compounds are those where $R^1$ is nitro, amino, aminoalkyl, hydroxy or methoxy; $R^2$ is hydroxy, carbonyloxy or halo; $R^2$ and $R^3$ combined together represent methylenedioxy or ethylenedioxy; $R^4$ is nitro; $R^5$ is ethyl, aminomethyl or piperizinomethyl; $R^6$ is carboxyl, carbomethoxy, carboethoxy, CHO group, cyano, or COOR' where R' is hydroxyethyl; trifluoroethyl; fluoroethyl; aminoethyl, substituted aminoethyl or acetamido where the amino group is unsubstituted pyrrolidino, piperidino, morphilino, diethylamino or diisopropylamino.

Representative compounds of formula 1 are:

1) 5-Carbomethoxymethyl CPT
2) 5-(2'-Oxopropyl) CPT
3) 5-Carboethoxymethyl CPT
4) 5-Carboxymethyl CPT
5) 9-Nitro-5-carbomethoxymethyl CPT
6) 9-Nitro-5-(2'oxopropyl) CPT
7) 9-Nitro-5-carboxymethyl CPT
8) 10-Hydroxy-5-carbomethoxymethyl CPT
9) 10-Hydroxy-5-(2'-oxopropyl) CPT 10) 10-Hydroxy-7-ethyl-5-(2'-oxopropyl) CPT
11) 10-Hydroxy-9-(N,N-dimethylaminomethyl)-5-carboxymethyl CPT
12) 5-Acetamido CPT
13) 5-(2'-Oxopyrrolidinoethyl) CPT
14) 5-(2'-Oxopiperidinoethyl) CPT
15) 5-Carboxymethyl camptothecin, fluoroethyl ester
16) 5-Carboxymethyl camptothecin, hydroxyethyl ester
17) 5-Carboxymethyl camptothecin, trifluoroethyl ester
18) 9-Methoxy-5-carboethoxymethyl CPT
19) 9-Hydroxy-5-carboethoxymethyl CPT
20) 9-Methoxy-5-carboxymethyl CPT
21) 5-(2'-Hydroxyethyl) CPT
22) 12-nitro-5-carbomethoxy methyl CPT
23) 12-nitro-5-(2'-oxopropyl) CPT where CPT refers to 20(S)-camptothecin In fact, most of the compounds prepared by the present invention have water solubility ranging from 1 mg to 5 mg per ml at 37° C. Further, several compounds prepared in the present invention exhibited good in vitro anti-cancer activity towards various human tumor cell lines, according to the results obtained from 60 human tumor cell line assay performed at National Cancer Institute (NCI), Bethesda, Md., U.S.A. The results shown in Tables 1 and 2 were obtained from conducting experiments according to U.S. National Cancer Institute (NCl) protocols as given below:

Each test compound was screened against a battery of 60 human cell lines obtained from eight organs. In a typical procedure, the cell suspensions that were diluted according to the particular cell type and the expected target cell density (5000–40,000 cells per well based on cell growth characteristics) were added into 96-well microtiter plates. Inoculates were allowed a preincubation period of 24 h at 37° C. for stabilization. Dilutions at twice the intended test concentrations were added at time zero in 100-μl aliquots to microtiter plate wells. Usually test compounds were evaluated at five 10-fold dilutions. The highest well concentration used in the test is $10^{-4}$ M. The cells are then incubated in the presence of drug (the test compound) for further 48 h in 5% $CO_2$ atmosphere and 100% humidity. At the end of this time, the adherent cells are fixed to the plate by means of trichloroacetic acid, and after a number of washes, the cell layer is treated with the protein stain Sulforhodamine B. The optical density which is proportional to protein mass, is then read by automated spectrophotometric plate readers at a wavelength of 515 nm. Readings are transferred to a microcomputer and fmal reports are generated using especially developed software.

TABLE 1

| S. NO. | COMPOUND | IC 50(μm)[a] |
|---|---|---|
| 1) | 5-Carbomethoxymethyl CPT | 16.2 |
| 2) | 5-(2'-Oxopropyl) CPT | 8.31 |
| 3) | 10-Hydroxy-5-carbomethoxymethyl CPT | 4.89 |
| 4) | 9-Nitro-5-(2'-oxopropyl) CPT | 1.00 |
| 5) | 9-Nitro-5-carbomethoxymethyl CPT | 15.8 |
| 6) | 5-Acetamido CPT | 26.9 |
| 7) | 9-Methoxy-5-carbomethoxy CPT | 16.2 |

[a]IC 50 = the mean value of the minimum drug concentration (μm) of the agent required to produce 50% cell growth inhibition (GI50) against NCI's 60 human tumor cell line assay.

TABLE 2

In vitro ANTI-CANCER activity data of EXAMPLES 2 and 4

| CELL PANEL | CELL LINE | EXAMPLE 2 | EXAMPLE 4 |
|---|---|---|---|
| LEUKEMIA | | | |
| | CCRF-CEM | 0.38 | 0.09 |
| | MOLT-4 | 0.77 | — |
| | HL 60 | — | 0.23 |
| | SR | 0.18 | 0.02 |
| NSLC | | | |
| | H 460 | 1.12 | 0.10 |
| | HOP 62 | 4.46 | 0.26 |
| | H 522 | 3.98 | |
| | H 23 | — | 0.24 |
| COLON | | | |
| | HCT 116 | 5.62 | 0.57 |
| | SW 620 | 6.02 | 0.07 |
| | HT 29 | — | 1.17 |
| CNS | | | |
| | SF-268 | 4.26 | — |
| | SF-539 | 3.89 | 0.26 |
| | SNB-19 | 6.45 | |
| | SF 295 | | 0.19 |
| RENAL | | | |
| | 786-O | 2.95 | 0.30 |
| | ACHN | 2.88 | 0.21 |
| | CAKI-1 | 2.63 | 0.21 |
| MELANOMA | | | |
| | LOX IMVI | — | 0.38 |
| | M 14 | — | 0.30 |
| | UACC 62 | — | 0.33 |
| BREAST | | | |
| | MCF-7 | 3.63 | — |
| | MCF7/ADR | 1.86 | — |
| | T 47D | 2.63 | — |

The data shown here refers to 50% Growth Inhibition (GI 50) values in μm concentrations.

All these compounds of the general formula 1 of the present invention, including the pharmaceutically acceptable salts thereof, and the composition containing them, are useful as anti-cancer and anti-viral agents. Administration of the active compositions of the formula 1, in pure form or in an appropriate pharmaceutical composition can be carried out via any of the accepted modes of administration for serving similar utilities. Thus, administration can be, for example, orally, nasally, parenterally or topically, in the form of solid, semi-solid, lyophilized powder, or liquid dosage forms, such as for example, tablets, suppositories, pills, capsules, powders, solutions, suspensions, emulsions, creams, lotions, aerosols, ointments, injections or the like, preferably, in unit dosage forms suitable, for simple administration of precise dosages. The compositions will include a conventional pharmaceutical carrier or excipient and an active compound of general formula 1 and, in addition, may include either medicinal agents, pharmaceutical agents, carriers, adjuvants, etc.

The invention is described in detail with specific examples given below which are provided by way of illustration only and should not be constructed to limit the scope of the invention.

EXAMPLES

Example 1

Preparation of 5-Carbomethoxymethylcamptothecin

To a solution of 100 mg of 5-hydroxycamptothecin of the formula 12 where $R^1=R^2=R^3=R^4=R^5=H$, dissolved in 12 ml of benzene and 0.1 ml of dry pyridine, in 5 ml of benzene was added 60 mg of carbomethoxymethylene triphenylphosphorane and stirred at 80° C. for 16 h. At the end, reaction mixture was acidified with 5% HCl and extracted with ethyl acetate. The organic extract was washed with water, brine and dried over anh.sodium sulfate. Concentration of the solvent and purification of the residue over silica gel column chromatography furnished 65 mg of 5-carbomethoxymethyl camptothecin of the formula 1; mp 235° C.; IR: (KBr): 3444, 2925, 1746(br), 1660, 1607, 1150, 721 cm$^{-1}$; $^1$H NMR (CDCl$_3$, 200 MHz): δ 8.41(s, 1H), 8.23(d, J=8.4 Hz, 1H), 7.92(d, J=8 Hz, 1H), 7.82 (t, J=7.4 Hz, 1H), 7.71–7.58(m,2H), 6.06(d, J=8 Hz,0.5H), 6.03 (d, J=8 Hz,0.5H), 5.71(d, J=16 hz 1H), 5.28(d, J=16 Hz, 1H), 3.92 (dd, J=17 Hz,3.4, 1H), 3.70(s, 3H), 3.35(dd, J=17 Hz, 7.6 Hz, 1H), 2.05–1.85(m, 2H), 1.05(t, 8 Hz, 3H), Mass (m/z): 420(M+1), 376, 361, 347, 317, 277, 201, 152, 95, 85

Example 2

Preparation of 5-(2'-Oxotpropyl)camptothecin

To a solution of 200 mg of 5-hydroxycamptothecin of the formula 12 where $R^1=R^2=R^3=R^4=R^5=H$, dissolved in 16 ml of toluene and 0.2 ml of dry pyridine, 140 mg of 1-triphenylphosphoranylidene-2-propanone in 8 ml of toluene was added and stirred at 100° C. for 16 h. At the end, reaction mixture was acidified with 5% HCl and extracted with ethyl acetate. The organic extract was washed with water, brine and dried over anh. sodium sulfate. Concentration of the solvent and purification of the residue over silica gel column chromatography furnished 140 mg of 5-(2'-oxopropyl)camptothecin of the formula 1; IR: (KBr): 3424, 1745, 1715, 1659, 1606, 1155 cm$^{-1}$; $^1$H NMR (CDCl$_3$, 200 MHz): δ 8.40 (s, 1H), 8.23 (d, J=8.4 Hz, 1H), 7.90 (d, J=8 Hz, 1H), 7.81( t, J=7.4 Hz, 1H), 7.71–7.58(m,2H), 6.11(d, J=7.2 Hz, 0.5H), 6.06(d, J=7.2 Hz,0.5H), 5.68(d, J=16 Hz, 1H), 5.26 (d, J=16 Hz, 1H), 4.27(dd, J=16.2 Hz,3.4 Hz, 1H), 3.75(s, 1 H, D$_2$O exchangeable), 2.81(dd, J=17 Hz, 7.6 Hz,0.5H), 2.71(dd, J=17 Hz, 7.6 Hz,0.5H), 2.24(s, 3H) 2.01–1.81(m,2H), 1.05(t, 8 Hz, 3H); Mass (m/z): 404(M+1), 391, 361, 347, 317, 231, 128, 107, 89.

Example 3

Preparation of 10-Hydroxy-5 carbomethoxymethylcamptothecin

To a solution of 100 mg of 10,5-dihydroxycamptothecin of the formula 12 where $R^2=OH$, $R^1=R^3=R^4=R^5=H$, dissolved in 20 ml of benzene was added 0.1 ml of dry pyridine and 60 mg of carbomethoxymethylene triphenylphosphane. The resulting solution was stirred at 80° C. mg for 16 h. At the end, reaction mixture was acidified with 5% HCl and extracted with ethyl acetate. The organic extract was washed with water, brine and dried over anh.sodium sulfate. Concentration of the solvent and purification of the residue over silica gel column chromatography furnished 65 mg of 10-hydroxy-5-carbomethoxymethylcamptothecin of the formula 1; mp: 153° C.: $^1$H NMR (CDCl3+DMSO-d6), δ 8.18 (s, 1H), 8.02(d, J=9 Hz, 1H), 7.58(s, 1H), 7.46(d, J=9 Hz, 1H), 7.18(s,1H), 5.95(dd, J=7.2 Hz,3.2 Hz, 0.5H), 5.90(dd, J=7.2 Hz, 3.2 Hz, 0.5H), 5.65( d, J=16 Hz, 1H), 5.25 (d, J=16 Hz, 1H), 3.84( dd, J=17 Hz, 3.4 Hz, 1H), 3.69(s, 3H), 3.05 (br s, 1 H, D$_2$O exchangeable), 2.91(dd, J=17 Hz, 7.6 Hz, 1H), 1.95(m,2H), 1.05(t, J=7 Hz, 3H); Mass (m/z): 436(M+1), 407, 392, 361, 347, 333, 247, 169, 107.

Example 4

Preparation of 9-Nitro-5-(2'-oxoprooyl) camptothecin

To a solution of 100 mg of 9-nitro-5-hydroxycamptothecin of the formula 12 where $R^1=NO_2$, $R^2=R^3=R^4=R^5=H$, dissolved in 10 ml of toluene wand 0.3 ml of dry pyridine, 80 mg of 1-triphenylphosphoranylidene-2-propanone in 5 ml of toluene was added and stirred at 100° C. for 16 h. At the end, reaction mixture was acidified with 5% HCl and extracted with ethyl acetate. The organic extract was washed with water, brine and dried over anh.sodium sulfate. Concentration of the solvent and purification of the residue over silica gel column chromatography furnished 80 mg of 9-nitro-5-(2'-oxopropyl)camptothecin of the formula 1; mp: 137° C. : IR: 3384, 1746, 1660, 1603, 1526, 1154 cm$^{-1}$; $^1$H NMR (CDCl$_3$): δ 9.21 (s, 1H), 8.53 (d, J=8.6 Hz, 1H), 8.46(d, J=8.6 Hz,1H), 7.91(t, J=8 Hz, 1H), 7.68(s,0.5H), 7.66(s, 0.5 SH), 6.04(dd, J=7.2 Hz, 3 Hz, 0.5H), 6.06 (dd, J=7.2 Hz, 3 Hz, 0.5H), 5.75( d, J=16 Hz, 0.5H), 5.73( d, J=16 Hz, 0.5H), 5.37( d, J=16 Hz, 0.5H), 5.24(d, J=16 Hz, 0.5H), 4.18 (dd, J=17 Hz, 3.4 Hz, 0.5H), 4.16(dd, J=17 Hz, 3.4 Hz, 0.5H), 3.85 (br s, 1 H, D$_2$O exchangeable), 3.35(dd, J=17 Hz, 7.6 Hz, 0.5H), 3.25 (dd, J=17 Hz, 7.6 Hz, 0.5H), 2.26(s, 3H), 1.96(m,2H), 1.12(t, J=7 Hz, 3H); Mass (m/z): 450(M+1), 419, 406, 376, 362, 332, 319, 304, 232, 159, 101.

Example 5

Preparation of 9-Nitro-5-carbomethoxymethylcamptothecin

To a solution of 150 mg of 9-nitro-5-hydroxycamptothecin of the formula 12 where $R^1=NO_2$, $R^2=R^3=R^4=R^5=H$, dissolved in 20 ml of benzene was added 0.4 ml of dry pyridine, 80 mg of carbomethoxymethylene triphenylphosphorane. The resulting solution was refluxed for 24 h. At the end, reaction niixture was acidified with 5% HCl and extracted with ethyl acetate. The organic extract was washed with water, brine and dried over anh-.sodium sulfate. Concentration of the solvent and purification of the residue over silica gel column chromatography furnished 110 mg of 9-nitro-5-carbomethoxymethyl camptothecin of the formula 1; mp: 140° C.: 1R: 3320, 1740, 1661, 1604, 1526, 1154, 1050, 740 cm$^{-1}$; $^1$H NMR (CDCl$_3$): δ 9.21 (s, 1H), 8.53(d, J=8.6 Hz, 1H), 8.46(d, J=8.6 Hz,1H), 7.91(t, J=8 Hz, 1H), 7.68(s,0.5H), 7.66(s, 0.5H), 6.19–6.03 (m,1H), 5.75 (d, J=16 Hz, 0.5H), 5.73( d, J=16 Hz, 0.5H), 5.37( d, J=16 Hz, 0.5H), 5.24( d, J=16 Hz, 0.5H), 3.82(d, J=17 Hz, 0.5H), 3.80(d, J=17 Hz, 0.5H), 3.85(br, s, 1 H, D$_2$O exchangeable), 3.68(s, 3H), 3.35(dd, J=17 Hz, 7.6 Hz, 0.5H), 3.25(dd, J=17 Hz, 7.6 Hz, 0.5H), 1.96(m,2H), 1.02(t, J=7 Hz, 3H); Mass (m/z): 465(M+1), 435, 422, 406, 391, 362, 332, 277, 169, 91.

Example 6

Preparation of 5-acetamidocamptothecin

Step 1: 5-Carbomethoxymethylcamptothecin of the formula 1 where $R=R^1=R^2=R^3=R^4=R^5=H$ and $R^6=COOMe$ was prepared as described in the example 1.

Step 2: 100 mg of 5-carbomethoxymethylcamptothecin of the formula 1 where $R=R^1=R^2=R^3=R^4=R^5=H$ and $R^6=COOMe$ was dissolved in 10 ml of 40% aqueous diethylamine and the contents were heated to reflux for 10 h. The reaction mixture was neutralized with 5% HCl and extracted with ethyl acetate. The organic extract was washed with water and brine. Evaporation of the solvent gave an oily residue which was purified over silica gel column chromatography using chloroform-acetone solvent mixture as eluent to obtain 65 mg of 5-acetamidocamptothecin of the formula 1, $R=R^1=R^2=R^3=R^4=R^5=H$ and $R^6$=CONH$_2$; mp: 250° C. : IR: 3230, 2927, 1746, 1658, 1584, 1402, 1152, 1050, 785, 541 cm$^{-1}$; Partial $^1$H NMR data in (CDCl$_3$+DMSO-d6): δ 6.05(d, J=8 Hz,0.5H) 5.95 (d, J=8 Hz, 0.5H), 5.62(d, J=16 Hz,1H), 5.26(d, J=16 Hz, 1H), 3.91 (dd, J=17 Hz,3.4 Hz, 1H), 3.70(s, 3H), 3.31(br s, D$_2$O exchangeable,1H), 3.35(dd, J=17 Hz,7.6 Hz,1H), 2.00–1.84 (m,2H), 1.07(t, J=8 Hz, 3H); Mass (m/z): 406(M+1), 362, 347, 333, 317, 305, 289, 262, 205, 159, 107, 84.

Example 7

Preparation of 5-(2'Oxopyrrolidinoethyl) camptothecin

Step 1: 5-Carbomethoxymethylcamptothecin of the formula 1 where R=R$^1$=R$^2$=R$^3$=R$^4$=R$^5$=H, R$^6$=COOMe was prepared as described in the example 1.

Step 2: 100 mg of 5-Carbomethoxymethylcamptothecin of the formula 1 where R=R=R$^2$=R$^3$=R$^4$=R$^5$=H and R$^6$ =COOMe was dissolved in 10 ml of pyrolidine and heated to reflux for 16 h. Excess pyrolidine was removed under vacuum and the residue was stirred with 20 ml of 10% HCl for 30min. Then, the aqueous solution was extracted with ethyl acetate and the organic layer was washed with brine and concentrated. The gummy solid was purified over column chromatography using chloroform-acetone solvent mixture to get 65 mg of 5-[2'-oxopyrrolidinoethyl] camptothecin of the formula 1, R=R$^1$=R$^2$=R$^3$=R$^4$=R$^5$=H, R$^6$=CON(CH$_2$)$_4$; mp: IR: 3387, 1747, 1659, 1615, 1446, 1408, 1141, 621 cm$^{-1}$: Partial $^1$H NMR data in CDCl$_3$: δ 6.22(d, J=8 Hz,0.5H) 6.15(d, J=8 Hz, 0.5H), 5.72 (d, J=16 Hz,1H), 5.26(d, J=16 Hz, 1H), 4.15(d, J=16 Hz, 1H), 3.81 (br s, D$_2$O exchangeable,1H), 3.71–3.18(m,4H), 2.51–2.29(m,1H), 2.15–1.85(m,6H), 1.18–1.02 (m,3H); Mass(m/z): 460(M+1), 416, 388, 360, 347, 316, 259, 231, 191, 128, 98, 83.

Example 8

Preparation of 5-(2'-Oxopiperidinoethyl) camptothecin

Step 1: 5-Carbomethoxymethylcamptothecin of the formula 1 where R=R$^1$=R$^2$=R$^3$=R$^4$=R$^5$=H, R$^6$=COOMe was prepared as described in the example 1.

Step 2: 125 mg of 5-Carbomethoxycamptothecin of the formula 1 where R=R$^1$=R$^2$=R$^3$=R$^4$=R$^5$=H and R$^6$ =COOMe was dissolved in 12 ml of piperine and heated to reflux for 16 h. Excess piperidine was removed under vacuum and the residue was stirred with 20 ml of 10% HCl for 30min. Then, the aqueous solution was extracted with ethyl acetate and the organic layer was washed with brine and concentrated. The resultant residue was purified over column chromatography using chloroform-acetone solvent mixture to get 75 mg of 5-[2'-oxopiperidinoethyl] camptothecin of the formula 1, R=R$^1$=R$^2$=R$^3$=R$^4$=R$^5$=H, R$^6$=CON(CH$_2$)$_5$; mp: 246° C. IR: 3385, 1749, 1649, 1614, 1450, 1404, 1228, 1154, 1050, 759, 559, 549 cm$^{-1}$: Partial $^1$H NMR in CDCl$_3$: δ 6.25(d, J=8 Hz, 0.5H) 6.15(d, J=8 Hz,0.5H), 5.75(d, J=16 Hz,1H), 5.29(d, J=16 Hz, 1H), 4.35–4.17(m, 1H), 3.81(br d, D$_2$O exchangeable, 1H), 3.85–3.21(m,4H), 2.54–2.34(m,1H), 2.05–1.85(m,6H), 1.75–1.38(m,6H), 1.18–1.02(m,3H); Mass(m/z): 474(M+1), 430, 388, 360, 344, 316, 287, 259, 231, 190, 126, 86.

Example 9

Preparation of 10-Hydroxy-5-(2'oxopropyl) camptothecin

To a solution of 100 mg of 10,5-dihydroxycamptothecin of the formula 12 where R$_2$=OH,R$^1$=R$^3$=R$^4$=R$^5$=H, dissolved in 10 ml of toluene was added 0.3 ml of dry triethylamine, 80 mg of 1-triphenylphosphoranylidene-2-propanone in 5 ml of toluene was added and stirred at 100° C. for 24 h. At the end, reaction mixture was acidified with 5% HCl and extracted with ethyl acetate. The organic extract was washed with water, brine and dried over anh.sodium sulfate. Concentration of the solvent and purification of the residue over silica gel column chromatography furnished 60 mg of 10-hydroxy-5-(2'oxopropyl) camptothecin of the formula 1; mp: 170° C. : $^1$H NMR (CDCl$_3$+DMSO-d6), : δ 8.18(s, 1H), 8.02(d, J=9 Hz, 1H), 7.58(s, 1H), 7.46(d, J=9 Hz, 1H), 7.18(s, 1H), 5.95 (dd, J=7.2 Hz,3.2 Hz, 0.5H), 5.90 (dd, J=7.2 Hz, 3.2 Hz, 0.5H), 5.65 (d, J=16 Hz, 1H), 5.25 (d, J=16 Hz, 1H), 4.18( dd, J=17 Hz, 3.4 Hz, 1H), 3.05(br s, 1h, D$_2$O exchangeable), 2.91–2.78(m, 1H), 2.26(s,3H), 1.95(m, 2H), 1.05(t, J=7 Hz, 3H); Mass (m/z): 408(M+1), 391, 375, 361, 333, 319, 279, 263, 175.

Example 10

Preparation of 9-methoxy-5-carbomethoxymethylcamptothecin

A solution of 150 mg of 9-Methoxy-5-hydroxycamptothecin of the formula 12 where R$^1$=OMe, R$^2$=R$^3$=R$^4$=R$^5$=H, dissolved in 12 ml of tetrahydrofuran was added to 1.5equiv., of sodium hydride in 5 ml of tetrahydrofuran followed by the addition of 60 mg of carbomethoxymethylene triphenylphosphorane and stirred at 25° C. for 16 h. At the end, reaction mixture was acidified with 5% HCl and extracted with ethyl acetate. The organic extract was washed with water, brine and dried over anh-.sodium sulfate. Concentration of the solvent and purification of the residue over silica gel column chromatography furnished 85 mg of 9-methoxy-5-carbomethoxymethyl camptothecin of the formula 1.

Example 11

Preparation of 5-Carboxymethyl camptothecin

Step 1: 5-Carbomethoxymethyl camptothecin of the formula 1 where R=R$^1$=R$^2$=R$^3$=R$^4$=R$^5$=H, R$^6$=COOMe was prepared as described in the example 1.

Step 2: To a methanolic solution of 100 mg of 5-carbomethoxy camptothecin was added 2 ml of 0.1 N sodium hydroxide solution and stirred at 25° C. for 10 h. Reaction mixture was acidified with dilute HCl and the aqueous layer extracted with 10% methanol- chloroform solvent mixture. Organic layer was washed with brine solution and the solvent concentrated to a minimum volume. The resulting residue was purified over silica gel column chromatography to get 75 mg of 5-carboxymethyl camptothecin of the formula 1, R=R$^1$=R$^2$=R$^3$=R$^4$=R$^5$=H and R$^6$=COOH. : mp: 240° C.; IR: 2973, 1755, 1655, 1579, 1560, 1154 cm$^{-1}$: $^1$H NMR in CDCl$_3$+DMSO-d6, 200 MHz): δ 8.6.0(s, 1H) 8.23(d, J=8 Hz, 1H), 8.15(d, J=8 Hz, 1H), 7.85(t, J=7.4 Hz, 1H), 7.68(t, J=7 Hz, 1H), 7.50(s,1H), 6.40(s, 1h, D$_2$O exchangeable), 6.06–5.85(m,1H), 5.55(d, J=16 Hz, 1H), 5.28(d, J=16 Hz, 1H), 4.15–3.92(dd, J=17 Hz,3.4 Hz, 1H), 3.35(dd, J=17 Hz, 7.6 Hz, 1H), 2.05–1.90 (m,2H), 1.05(t, 8 Hz, 3H); $^{13}$C NMR (50 MHz, DMSO): δ 172.5, 170.9, 157.2, 152.2, 150.2, 150.0 148.1, 145.6, 133.2, 130.7, 130.4, 129.0, 128.6, 127.9, 127.6, 119.8, 96.8, 83.6, 72.4, 65.3, 59.0, 34.3, 33.8, 30.3, 7.8; Mass(m/z): 406(M+1), 378, 362, 348, 319, 277, 191, 111.

Example 12

Preparation of 10-hydroxy-5-carboxymethyl camptothecin

Step 1: 10-Hydroxy-5-carbomethoxymethyl camptothecin of the formula 1 where R$^2$=OH, R=$R^1$=$R^2$=$R^3$=$R^4$=$R^5$=H, $R^6$=COOMe was prepared as described in the example 3.

Step 2: To a methanolic solution of 150 mg of 10-hydroxy-5-carbomethoxymethyl camptothecin was added 3 ml of 0.1 N sodium hydroxide solution and stirred at 25° C. for 10 h. Reaction mixture was acidified with dilute HCl and extracted the aqueous layer with 10% methanol-chloroform solvent mixture. Organic layer was washed with brine solution and concentrated the solvent to a minimum volume. The resulting residue was purified over silica gel column chromatography to get 105 mg of 10-hydroxy-5-carboxymethyl camptothecin of the formula 1, $R^2$=OH, R=$R^1$=$R^3$=$R^4$=$R^5$=H and $R^6$=COOH.

Example 13

Preparation of 5-Carboxymethyl camptothecin, fluoroethyl ester

Step 1: 5-Carboxymethyl camptothecin of the formula 1 where R=$R^1$=$R^2$=$R^3$=$R^4$=$R^5$=H, $R^6$=COOH was prepared as described in the example 11.

Step 2: 100 mg of 5-carboxymethyl camptothecin of the formula 1 where R=$R^1$=$R^2$=$R^3$=$R^4$=$R^5$=H, $R^6$=COOH, dissolved in 15 ml of dichloroethane was treated with 0.5 ml of 2-fluoroethanol and the contents heated to 80° C. for 10 h in the presence of cat. amount of sulfuric acid. Reaction mixture was neutralized with pyridine and diluted with ethyl acetate. Organic layer was washed, brine and dried over sodium sulfate. Concentration of the solvent and purification of the resulting residue over silica gel column produced 5-carboxymethyl camptothecin, fluoroethyl ester of the formula 1 R=$R^1$=$R^2$50 $R^3$=$R^4$=$R^5$=H and $R^6$=COCH$_2$CH$_2$F; mp: 220° C.; IR: 3444, 1742, 1660, 1599, 1158, cm$^4$: $^1$H NMR in (CDCl$_3$, 200 MHz): δ 8.41(s, 1H) 8.20(d, J=8.4 Hz, 1H), 7.90(d, J=8 Hz, 1H), 7.80(t, J=7.4 Hz, 1H), 7.65(t, J=7 Hz,1H), 7.66(s, 1H), 6.15–5.95(m,1H), 5.68(d, J=16 Hz, 1H), 5.25(d, J=16 Hz, 1H), 4.70–4.20(m.4H), 4.10–3.80(m,1H), 3.75 (1 s, 1 H, D$_2$O exchangeable), 3.20–2.85(m,1H) 2.0514 1.80(m,2H), 1.05(t, 8 Hz, 3H); Mass(m/z): 452(M+1), 408, 389, 361, 317.

Example 14

Preparation of 5-Carboxymethyl camptothecin, hydroxyethyl ester

Step 1: 5-Carboxymethyl camptothecin of the formula 1 where R=$R^1$=$R^2$=$R^3$=$R^4$=$R^5$=H, $R^6$=COOH was prepared as described in the example 11.

Step 2: 150 mg of 5-carboxymethyl camptothecin of the formula 1 where R=$R^1$=$R^2$=$R^3$=$R^4$=R=H and $R^6$=COOH, dissolved in 15 ml of dichloroethane was treated with 0.5 ml of ethylene glycol and heated the contents to 80° C. for 8 h in the presence of cat. amount of sulfuric acid. Reaction mixture was neutralized with pyridine and diluted with ethyl acetate. Organic layer was washed, brine and dried over sodium sulfate. Concentration of the solvent and purification of the resulting residue over silica gel column produced 112 mg of 5-carboxymethyl camptothecin, hydroxyethyl ester of the formula 1 where R=$R^1$=$R^2$=$R^3$=$R^4$=$R^5$=H and $R^6$=COOCH$_2$CH$_2$OH; mp: 210° C.; IR: 3336, 1737, 1658, 1593, 1158, cm$^{-1}$: $^1$H NMR in (CDCl$_3$, 200 MHz): δ 8.43(s, 1H) 8.22(d, J=8.4 Hz, 1H), 7.93(d, J=8 Hz, 1H), 7.84(t, J=7.4 Hz, 1H), 7.68(t, J=7 Hz, 1H), 7.66(s,1H), 6.15–6.00(m,1H), 5.69(d, J=16 Hz, 1H), 5.25(d, J=16 Hz, 1H), 4.50–4.20(m,2H), 4.10–3.90–3.55(m,3H), 3.45(s,1 H, D$_2$O exchangeable), 3.20–3.00(m,1H), 2.05–1.80(m,2H), 1.05(t, 8 Hz, 3H); Mass (m/z): 450 (M+1), 432, 406, 361, 317, 218.

Example 15

Preparation of 5-Carboxymethyl camptothecin, trifluoroethyl ester

Step 1: 5-Carboxymethyl camptothecin of the formula 1 where R=$R^1$=$R^2$=$R^3$=$R^4$=$R^5$=and $R^6$=COOH was prepared as described in the example 11.

Step 2: 80 mg of 5-carboxymethyl camptothecin of the formula 1 where R=$R^1$=$R^2$=$R^3$=$R^4$=$R^5$=H and $R^6$=COOH, suspended in 15 ml of trifluoroethanol and heated the contents heated to 70° C. for 24 h in the presence of cat. amount of sulfuric acid. Excess trifluoroethanol was distilled off and the residue was diluted with ethyl acetate. Organic layer was washed with water, brine and dried over sodium sulfate. Concentration of the solvent and purification of the resulting residue over silica gel column produced 35 mg of 5-carboxymethyl camptothecin, trifluoroethyl ester of the formula 1 where R=$R^1$=$R^2$=$R^3$=$R^4$=$R^5$=H and $R^6$=COOCH$_2$CF$_3$; mp: 196° C.; IR: 3434, 1757, 1733, 1644, 1615, 1151 cm$^{-1}$: $^1$H NMR in (CDCl3, 200 MHz): δ 8.40(s, 1H) 8.25(d, J=8.4 Hz, 1H), 7.95(d, J=8 Hz, 1H), 7.84(t, J=7.4 Hz, 1H), 7.65(t, J=7 Hz, 1H), 7.66(s,1H), 6.10–5.95(m,1H), 5.68(d, J=16 Hz, 1H), 5.25(d, J=16 Hz, 1H), 4.65–4.35(m,2H), 4.10–3.85(m,1H), 3.80(s,1 H, D$_2$O exchangeable), 3.35–3.05(m,1H); 2.00–1.75(m,2H), 1.05(t, 8 Hz, 3H); Mass(m/z): 488 (M+1), 459, 444, 361, 317.

Example 16

Preparation of 9-Nitro-5-carboxymethyl camptothecin

Step 1: 9-Nitro-5-carbomethoxy camptothecin of the formula 1 where $R^1$=NO$_2$, R=$R^2$=$R^3$=$R^4$=$R^5$=H, $R^6$=COOMe was prepared as described in the example 5.

Step 2: To a methanolic solution of 120 mg of 9-nitro-5-carbomethoxymethyl camptothecin was added 2 ml of 0.1 N sodium hydroxide solution and stirred at 25° C. for 10 h. Reaction mixture was acidified with dilute HCl and the aqueous layer was extracted with 10% methanol-chloroform solvent mixture. Organic layer was washed with brine solution and the solvent concentrated to a minimum volume. The resulting residue was purified over silica gel column chromatography to get 55 mg of 9-nitro-5-carboxymethyl camptothecin of the formula 1 where $R^1$=NO$_2$, $R^2$=$R^3$=$R^4$=$R^5$=H and $R^6$=COOH.; IR: 3344, 2920, 1738, 1720, 1660, 1600, 1528, 1384, 1159; $^1$H NMR in (CDCl$_3$): δ 9.21(s, 1H) 8.53(d, J=8.6 Hz, 1H), 8.46 (d, J=8.6 Hz,1H), 7.91(t, J=8 Hz, 1H), 7.68(s, 0.5H), 7.66(s,0.5H), 6.19–6.03(m,1H), 5.81(br s, 1 H, D$_2$O exchangeable), 5.6 d, J=16 Hz, 1H), 5.37 (d, J=16 Hz, 0.5H), 5.27( d, J=16 Hz, 1H), 4.01–3.859(m,1H), 3.25(br s, 1 H, D$_2$O exchangeable), 3.10-2.81(m,1H), 1.96(m,2H), 1.02(t, J=7 Hz, 3H).

Example 17

Preparation of 5-(1'-carboxyethyl) camptothecin, methoxyethyl ester

Step 1: 5-Carbomethoxy camptothecin of the formula 1 where R=$R^1$=$R^2$=$R^3$=$R^4$=$R^5$=H and $R^6$=COOH was prepared as described in the example 11.

Step 2: 200 mg of 5-carboxymethyl camptothecin of the formula 1 where R=$R^1$=$R^2$=$R^3$=$R^4$=$R^5$=H and R⁶=COOH, dissolved in 2 ml of dichloroethane was treated with of 0.6 ml of ethylene glycol monomethylether and the contents heated to 80° C. for 10 h in the presence of cat. amount of sulfuric acid. Reaction was quenched with pyridine and diluted with ethyl acetate. Organic layer was washed with water, brine and dried over sodium sulfate. Concentration of the solvent and purification of the resulting residue over silica gel column produced 132 mg of 5-carboxymethyl camptothecin, methoxyethyl ester of the formula 1 where R=R¹=R²=R³=R⁴=R⁵=H and R⁶=COOCH₂CH₂OMe;

Step 3: 100 mg of 5-carboxymethyl camptothecin, methoxyethyl ester of the formula 1 where R=R¹=R²=R³=R⁴=R⁵=H and R⁶=COOCH₂CH₂OMe; was dissolved on 10 ml of tetrahydrofuran and added to lithium hexamethyldisilazide solution in tetrahydrofuran, precooled to –78° C. After 20 min, 0.5 ml of methyl iodide was added to it and continued stirring for 30 min. more and neutralized with brine solution. The organic layer was extracted with ethyl acetate and dried over anh. sodium sulfate. Concentration of the solvent and purification of the residue over silica gel column afforded 50 mg of 5-(1'carboxyethyl) camptothecin, methoxyethyl ester of the formula 1 where R=Me, R=R¹=R²=R³=R⁴=R⁵=H and R⁶=CO OCH₂ CH₂ OMe.

What is claimed is:

1. A compound of formula 1,

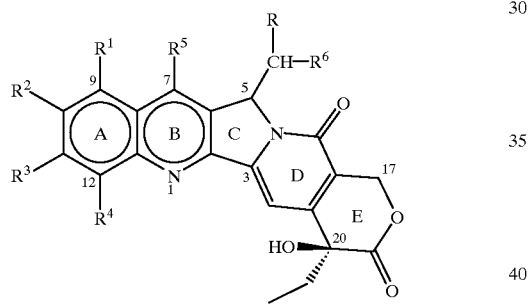

wherein R¹, R², R³, and R⁴ are hydrogen; or represent a group selected from hydroxy, lower alkoxy, lower alkanoyl, nitro, cyano, halo, carboxy, amino, substituted amino, wherein the amino group is mono or disubstituted wherein the substituent is selected from lower alkyl, lower haloalkyl, benzyl, benzoyl, carboxy, amido, or lower alkylamino; lower alkyl, or substituted lower alkyl wherein the substituent is selected from hydroxy, lower haloalkyl, benzyl, lower alkoxy, benzyloxy, cyano, nitro, amido, amino or lower alkylamino; each of R¹, R², R³, and R⁴ are not the same except where each of R¹, R², R³, and R⁴ are hydrogen; or R² and R³ together represent —O—(CH₂)ₙ—O— where n=1 or 2;

R⁵ represents hydrogen, lower alkyl, substituted lower alkyl, wherein the substituent is selected from hydroxy, halogen, lower alkoxy, benzyloxy, carboxy, amido or amino wherein the amido or amino group is mono or disubstituted wherein the substituent is selected from lower alkyl, lower haloalkyl, benzyl, or benzoyl, when the amido or amino group is disubstituted the substituents are independent or together with the linking nitrogen atom form a saturated 5 or 6 membered heterocyclic ring of formula (A);

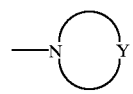

where Y represents O, S, NH or CH₂ when formula (A) is a 5-membered ring and Y represents CH₂ when formula (A) is a 6-membered ring or R⁵ represents lower aralkyl, where the aryl group is selected from phenyl, biphenyl or naphthyl;

when R represents hydrogen, R⁶ represents cyano, nitro, thio, thioalkyl, phenylthio; amido or amino group in which the amido or amino group can be unsubstituted, mono or disubstituted wherein when the amido or amino group is mono or disubstituted the substituent is selected from hydroxy, lower alkyl, lower haloalkyl, benzyl, benzoyl, lower alkoxy, carboxy, amido, amino or lower alkylamino, when the amido or amino group is disubstituted the substituents are independent or together with the linking nitrogen atom form a saturated 5 or 6 membered heterocyclic ring of formula (A)

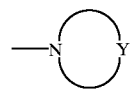

where Y represents O, S, NH or CH₂ when formula (A) is a 5-membered ring and Y represents CH₂ when formula (A) is a 6-membered ring; phenoxy; or benzoyl wherein the phenyl group can be unsubstituted or substituted with mono, di or trisubstituents selected from hydroxy, lower alkyl, lower haloalkyl, phenyl, benzyl, halogen, lower alkoxy, thioalkoxy, benzyloxy, carboxy, cyano, nitro, amido, amino or lower alkylamino; cycloalkyl or cycloalkyl lower alkyl where the cyclic ring has 3 to 7 ring atoms all of said rings atoms being carbon atoms; lower alkyl group substituted with a saturated 5 or 6 membered heterocyclic ring of formula (B)

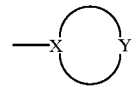

where X represents CH or N and Y represents O, S, NH, or CH₂ when formula (B) is a 5 membered ring wherein at least one of X or Y is a heteroatom or X represents N and Y represents CH₂ when formula (B) is a 6 membered ring; lower alkanoyl; substituted lower alkyl or substituted lower alkenyl, wherein the substituent is selected from halogen, hydroxy, benzyloxy, lower alkoxy, aryloxy, carboxy, cyano, thio, thioalkyl, thioaryl, aryl wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazole or imidazole; nitro, amido or amino wherein the amido or amino group is unsubstituted, or mono or disubstituted wherein the substituent is selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic of formula (A)

(A)

where Y represents O, S, NH or $CH_2$ when formula (A) is a 5-membered ring and Y represents $CH_2$ when formula (A) is a 6-membered ring, or $R^6$ represents COOR' where R' represents hydrogen, lower alkyl, substituted lower alkyl, wherein the substituent is selected from phenyl, benzyl, halogen, lower alkoxy, thioalkoxy, benzyloxy, carboxy, cyano, nitro, amido, amino or lower alkylamino, or lower aralkyl wherein the aryl group is phenyl, biphenyl or napthyl;

when R represents lower alkyl, lower alkenyl, lower alkanoyl, substituted lower alkyl wherein the substituent is selected from hydroxy, lower haloalkyl, benzyl, lower alkoxy, benzyloxy, cyano, nitro, amido, amino or lower alkylamino; substituted lower alkanoyl, phenyl, benzyl or benzoyl in which the phenyl group may be unsubstituted or substituted; or lower alkoxycarbonyl; $R^6$ represents benzoyl, cyano, nitro, lower alkanoyl; or $R^6$ represents COOR' group in which R' represents hydrogen, lower alkyl, lower aralkyl or substituted lower alkyl wherein the substituent is selected from hydroxy, lower haloalkyl, benzyl, lower alkoxy, benzyloxy, cyano, nitro, amido, amino or lower alkylamino.

2. A compound of formula 13,

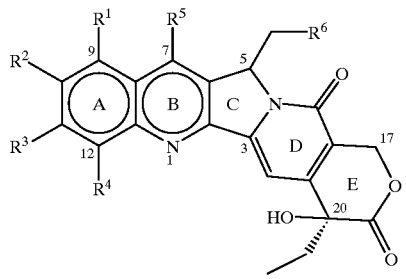

where $R^1, R^2, R^3, R^4$ and $R^5$ are hydrogen, and $R^6$ represents COOH.

3. A compound of formula 13,

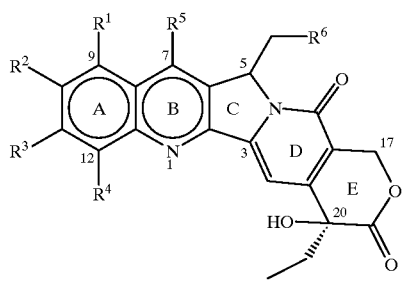

where $R^1$, $R^3$, $R^4$ and $R^5$ are hydrogen, $R^2$ represents hydroxyl and $R^6$ represents COOH.

4. A compound of formula 13,

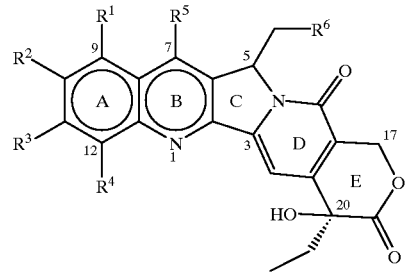

where $R^1$ represents nitro, $R^2$, $R^3$, $R^4$ and $R^5$ represent hydrogen and $R^6$ represents $COCH_3$.

5. A compound of formula 13,

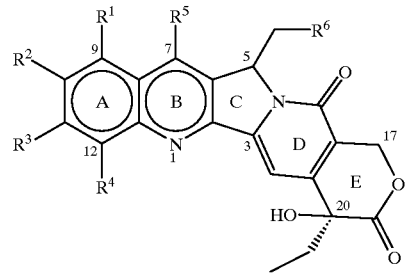

where $R^1, R^2, R^3, R^4$ and $R^5$ are hydrogen and $R^6$ represents $COOCH_2CH_2OH$.

6. A compound of formula 1,

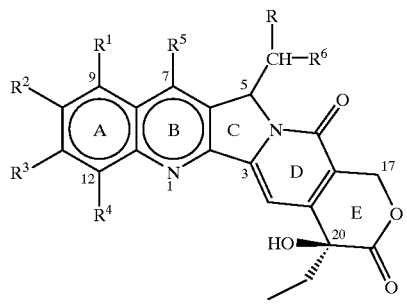

where $R^1, R^2, R^3, R^4$ and $R^5$ are hydrogen and $R^6$ represents $COOCH_2CF_3$ and R represents methyl.

7. Compounds of formula 1 as claimed in claim 1 wherein R, $R^1, R^2, R^3, R^4, R^5$ and $R^6$ have the meaning described in claim 6 as a mixture of two diastereomers having 20(S), 5(R) and 20(S), 5(S) configurations.

8. A compound of formula 1 as claimed in claim 1 having 20(S), 5(R) configuration substantially free from 20(S), 5(S) stereoisomer, wherer R, $R^1, R^2, R^3, R^4, R^5$ and $R^6$ have the meaning described in claim 1.

9. A compound of formula 1 as claimed in claim 1 having 20(S), 5(S) configuration, substantially free from the 20(S), 5(R) stereoisomer, where R, $R^1, R^2, R^3, R^4, R^5$ and $R^6$ have the meaning described in claim 1.

10. A pharmaceutical composition comprising an effective amount of a compound of formula 1 as defined in claim 1 or a pharmaceutically acceptable salt thereof and a pharmaceutically acceptable non-toxic excipient, diluent or carrier.

11. A method for treating cancer susceptible to camptothecin treatment or leukemia comprising administering to a patient in need thereof an effective amount of a compound of formula 1 as defined in claim 1 or a pharmaceutically acceptable salt thereof.

12. A compound selected from:
5-Carbomethoxymethyl CPT,
5-(2'-Oxopropyl) CPT,
5-Carboethoxymethyl CPT,
5-Carboxymethyl CPT,
9-Nitro-5-carbomethoxymethyl CPT,
9-Nitro-5-(2'-oxopropyl) CPT,
9-Nitro-5-carboxymethyl CPT,
10-Hydroxy-5-carbomethoxymethyl CPT,
10-Hydroxy-5-(2'-oxopropyl) CPT,
10-Hydroxy-7ethyl-5-(2'-oxopropyl) CPT,
10-Hydroxy-9-(N,N-dimethylaminomethyl)-5-carboxymethyl CPT,
5-Acetamido CPT,
5-(2'-Oxopyrrolidinoethyl) CPT,
5-(2'-Oxopiperidinoethyl) CPT,
5-Carboxymethyl camptothecin, fluoroethyl ester,
5-Carboxymethyl camptothecin, hydroxyethyl ester,
5-Carboxymethyl camptothecin, trifluoroethyl ester,
9-Methoxy-5-carboethoxymethyl CPT,
9-Hydroxy-5-carboethoxymethyl CPT,
9-Methoxy-5-carboethoxymethyl CPT,
5-(2'-Hydroxyethyl) CPT,
12-nitro-5-carbomethoxy methyl CPT, and
12-nitro-5-(2'-oxopropyl) CPT
where CPT is 20(S)-camptothecin.

* * * * *

UNITED STATES PATENT AND TRADEMARK OFFICE
CERTIFICATE OF CORRECTION

PATENT NO. : 6,214,836 B1
DATED : April 10, 2001
INVENTOR(S) : Subrahmanyam Duvvuri, et al.

It is certified that error appears in the above-identified patent and that said Letters Patent is hereby corrected as shown below:

Title page,
Item [63], "17, 1996, now Pat. No. 6,028,173" should read -- 5, 1996 --.

Column 1,
Lines 5-6, "17, 1996, now U.S. Pat. No. 6,028,173" should read -- 5, 1996 --.

Signed and Sealed this

Ninth Day of October, 2001

Attest:

NICHOLAS P. GODICI
Attesting Officer *Acting Director of the United States Patent and Trademark Office*